US011802280B2

(12) United States Patent
Jiang et al.

(10) Patent No.: US 11,802,280 B2
(45) Date of Patent: Oct. 31, 2023

(54) ENZYME FOR SYNTHESIZING HYDROXYL ACETALDEHYDE AND/OR 1,3-DIHYDROXYACETONE BY CATALYZING FORMALDEHYDE, AND APPLICATIONS THEREOF

(71) Applicant: Tianjin Institute of Industrial Biotechnology, Chinese Academy of Sciences, Tianjin (CN)

(72) Inventors: Huifeng Jiang, Tianjin (CN); Xiaoyun Lu, Tianjin (CN); Yuwan Liu, Tianjin (CN); Yiqun Yang, Tianjin (CN); Lina Lu, Tianjin (CN); Sheng Yang, Tianjin (CN); Junran Gou, Tianjin (CN)

(73) Assignee: Tianjin Institute of Industrial Biotechnology, Chinese Academy of Sciences, Tianjin (CN)

( * ) Notice: Subject to any disclaimer, the term of this patent is extended or adjusted under 35 U.S.C. 154(b) by 221 days.

(21) Appl. No.: 16/483,716

(22) PCT Filed: Feb. 12, 2018

(86) PCT No.: PCT/CN2018/076466
§ 371 (c)(1),
(2) Date: Aug. 5, 2019

(87) PCT Pub. No.: WO2018/153306
PCT Pub. Date: Aug. 30, 2018

(65) Prior Publication Data
US 2020/0024590 A1 Jan. 23, 2020

(30) Foreign Application Priority Data
Feb. 22, 2017 (CN) .................. 201710096307.X

(51) Int. Cl.
*C12N 9/88* (2006.01)
*C12P 7/24* (2006.01)
*C12P 7/28* (2006.01)
*C12P 9/00* (2006.01)
*C12P 19/32* (2006.01)

(52) U.S. Cl.
CPC .................. *C12N 9/88* (2013.01); *C12P 7/24* (2013.01); *C12P 7/28* (2013.01); *C12P 9/00* (2013.01); *C12P 19/32* (2013.01); *C12Y 401/01007* (2013.01)

(58) Field of Classification Search
None
See application file for complete search history.

(56) References Cited

FOREIGN PATENT DOCUMENTS

| CN | 105132400 A | 12/2015 | | |
|---|---|---|---|---|
| CN | 106916794 A | 7/2017 | | |
| WO | WO 2015144447 A1 | 10/2015 | | |
| WO | WO-2015181074 A1 * | 12/2015 | ..... | C12Y 401/02009 |

OTHER PUBLICATIONS

Andrews et al., "Using site-saturation mutagenesis to explore mechanism and substrate specificity in thiamin diphosphatedependent enzymes," FEBS J. 280:6395-6411, 2013 (Year: 2013).*
Singh et al., Curr. Protein Pept. Sci. 18:1-11, 2017 (Year: 2017).*
Zhang et al., Structure 26:1474-1485, 2018 (Year: 2018).*
Lingen et al., Protein Engineer. 15:585-593, 2002 (Year: 2002).*
Machine translation of CN105132400A, obtained from Espacenet, 9 pages, Aug. 2021 (Year: 2021).*
International Search Report received in PCT Application No. PCT/CN2018/076466, dated May 11, 2018.

* cited by examiner

*Primary Examiner* — David Steadman
(74) *Attorney, Agent, or Firm* — KNOBBE, MARTENS, OLSON & BEAR, LLP

(57) ABSTRACT

An enzyme synthesizes hydroxyl acetaldehyde and/or 1,3-dihydroxyacetone by catalyzing formaldehyde. Site-directed mutation of benzoylformate decarboxylase (BFD) creates a mutant of the enzyme, which can polymerize the formaldehyde, A phosphoketalose (F/XPK) generates acetyl phosphoric acid from the hydroxyl acetaldehyde or 1,3-dihydroxyacetone (DHA). Combination with phosphotransacetylase (Pta) provides a route from the formaldehyde to acetyl coenzyme A in three steps.

15 Claims, 7 Drawing Sheets
Specification includes a Sequence Listing.

ENZYME FOR SYNTHESIZING HYDROXYL ACETALDEHYDE AND/OR 1,3-DIHYDROXYACETONE BY CATALYZING FORMALDEHYDE, AND APPLICATIONS THEREOF

CROSS-REFERENCED TO RELATED APPLICATIONS

This application is the U.S. National Phase under 35 U.S.C. § 371 of International Application No. PCT/CN2018/076466, filed Feb. 12, 2018, designating the U.S., and published in Chinese as WO 2018/153306 A1 on Aug. 30, 2018, which claims priority to Chinese Patent Application No. 201710096307.X, filed Feb. 22, 2017, the entire contents of which are incorporated herein by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 31056376_1.TXT, the date of creation of the ASCII text file is Aug. 1, 2019, and the size of the ASCII text file is 26,780 bytes.

TECHNICAL FIELD

The present invention relates to the field of biotechnology, in particular, to enzyme for synthesizing hydroxyl acetaldehyde and/or 1,3-dihydroxyacetone by catalyzing formaldehyde and applications thereof.

BACKGROUND

In nature, methylotrophic bacteria can use C1 source to synthesize metabolites which are necessary to their growth. Methylotrophic bacteria mainly have three pathways to assimilate formaldehyde: Ribulose Monophosphate Pathway (RuMP), Serine Cycle Pathway and Calvin-Benson-Bassham(CBB) Cycle Pathway after complete oxidation of formaldehyde, respectively. In Ribulose Monophosphate Pathway (RuMP), three molecules of formaldehyde are condensed to one molecule of pyruvic acid, followed by decarboxylation to form acetyl coenzyme A and $CO_2$. This process has a carbon availability of 67%. Serine Cycle Pathway needs ATP supplied by the outside to drive reactions adverse to thermodynamics. Likewise, it also needs extra ATP for fixation of $CO_2$ by using Calvin-Benson-Bassham (CBB) Cycle after formaldehyde has been completely oxidized into $CO_2$. Extra carbons have to be consumed for the supply of ATP to drive oxidative phosphorylation. A reductive acetyl coenzyme A pathway present in *Clostridium ljungdahlii* is capable of assimilating carbon dioxide from oxidated formaldehyde to generate acetyl coenzyme A, with no carbon loss in this process. However, since such pathway is extremely sensitive to oxygen, it is difficult for use in other species. An artificial synthesis pathway—Methanol Condensation Cycle (MCC) consists of Ribulose Monophosphate Pathway (RuMP) and Non-Oxidative Glycolysis (NOG), and such combined pathway neither has any carbon loss nor needs a supply of ATP. In Formose Pathway, three molecules of formaldehyde are condensed to 1,3-dihydroxyacetone, and then 1,3-dihydroxyacetone is phosphorylated to DHAP (dihydroxyacetone phosphate). A carbon loss likewise appears in this process where DHAP is converted to acetyl coenzyme A.

SUMMARY

One object of the present invention is to provide a benzoylformate decarboxylase BFD mutant protein and applications thereof.

In first aspect, the present invention seeks to protect any one of the following methods:

(1) a method for producing acetyl phosphoric acid by using formaldehyde can comprise the following steps of: (1) preparing hydroxyl acetaldehyde and/or 1,3-dihydroxyacetone by using formaldehyde as a substrate; (2) preparing acetyl phosphoric acid by using hydroxyl acetaldehyde and/or 1,3-dihydroxyacetone as a substrate.

Further, in said method, said "preparing hydroxyl acetaldehyde and/or 1,3-dihydroxyacetone by using formaldehyde as a substrate" is catalyzing formaldehyde to be condensed to hydroxyl acetaldehyde and/or 1,3-dihydroxyacetone with said BFD mutant protein in the second aspect below, using formaldehyde as a substrate. Said "preparing acetyl phosphoric acid by using hydroxyl acetaldehyde and/or 1,3-dihydroxyacetone as a substrate" is catalyzing hydroxyl acetaldehyde and/or 1,3-dihydroxyacetone to generate acetyl phosphoric acid with phosphoketolase (F/XPK) protein, using hydroxyl acetaldehyde and/or 1,3-dihydroxyacetone as a substrate.

(2) a method for producing acetyl coenzyme A by using formaldehyde can comprise the following steps of: (1) preparing hydroxyl acetaldehyde and/or 1,3-dihydroxyacetone by using formaldehyde as a substrate; (2) preparing acetyl phosphoric acid by using hydroxyl acetaldehyde and/or 1,3-dihydroxyacetone as a substrate; (3) preparing acetyl coenzyme A by using acetyl phosphoric acid as a substrate.

Further, in said method, said "preparing hydroxyl acetaldehyde and/or 1,3-dihydroxyacetone by using formaldehyde as a substrate" is catalyzing formaldehyde to be condensed to hydroxyl acetaldehyde and/or 1,3-dihydroxyacetone with said BFD mutant protein in the second aspect below, using formaldehyde as a substrate. Said "preparing acetyl phosphoric acid by using hydroxyl acetaldehyde and/or 1,3-dihydroxyacetone as a substrate" is catalyzing hydroxyl acetaldehyde and/or 1,3-dihydroxyacetone to generate acetyl phosphoric acid with F/XPK protein, using hydroxyl acetaldehyde and/or 1,3-dihydroxyacetone as a substrate. Said "preparing acetyl coenzyme A by using acetyl phosphoric acid as a substrate" is catalyzing acetyl phosphoric acid to generate acetyl coenzyme A with phosphotransacetylase, using acetyl phosphoric acid as a substrate.

(3) a method for preparing hydroxyl acetaldehyde and/or 1,3-dihydroxyacetone, comprises the following steps of: catalyzing formaldehyde to be condensed to hydroxyl acetaldehyde and/or 1,3-dihydroxyacetone with said BFD mutant protein in the second aspect below, using formaldehyde as a substrate.

In the above several methods in the present invention, the amino acid sequence of said F/XPK protein particularly is SEQ ID No.3. Correspondingly, the coding gene sequence of said F/XPK protein is SEQ ID No.4. The amino acid sequence of said phosphotransacetylase particularly is SEQ ID No.5. Correspondingly, the coding gene sequence of said phosphotransacetylase is SEQ ID No.6.

In the above several methods, a bio-enzyme (such as said BFD mutant protein, said F/XPK protein and/or phosphotransacetylase) catalyzing a substrate to generate a corresponding product particularly can perform its catalyzing function in the form of a crude enzyme liquid, lyophilized powders of a crude enzyme liquid, a pure enzyme or whole cells.

Further, all said crude enzyme liquid, lyophilized powders of a crude enzyme liquid and a pure enzyme can be obtained from preparation in accordance with the method comprising the following steps: expressing said bio-enzyme in a host cell, and obtaining a recombinant cell; lysing said recombinant cell to obtain said crude enzyme liquid, lyophilized powders of said crude enzyme liquid or pure enzyme. Said whole cells can be obtained from preparation in accordance with the method comprising the following steps: expressing said bio-enzyme in a host cell, and the obtained recombinant cell is said whole cell.

Still further, said recombinant cell can be obtained from preparation in accordance with the method comprising the following steps: introducing a nucleic acid molecule capable of expressing said bio-enzyme into said host cell, and then obtaining said recombinant cell expressing said bio-enzyme after induction culture.

More particularly, said "a nucleic acid molecule capable of expressing said bio-enzyme" can be introduced into said host cell in the form of a combinant vector; said recombinant vector is a bacterial plasmid (such as an expression vector expressed in bacteria based on a T7 promoter, in particular, for example pET-28a etc.), phage, a yeast plasmid (such as a vector of the YEp series etc.) or a retrovirus packaging plasmid carrying the coding gene of said bio-enzyme. Said host cell is a prokaryotic cell or a lower eukaryotic cell.

wherein, said prokaryotic cell particularly can be bacteria; said lower eukaryotic cell particularly can be a yeast cell.

In one example of the present invention, said bacteria particularly are *E. coli*.

In second aspect, the present invention seeks to protect a BFD mutant protein.

The BFD mutant protein provided by the present invention is a protein obtained by performing one or more mutations on the amino acid residues of the BFD amino acid sequence in a range of 10 Å or 8 Å or 5 Å or 3 Å away from the active center.

Further, compared with the BFD amino acid sequence, said BFD mutant protein can have mutations at or merely at any one or more of the following positions: position 25, position 26, position 86, position 87, position 109, position 110, position 184, position 236, position 281, position 282, position 374, position 376, position 377, position 379, position 380, position 397, position 401, position 430, position 457, position 459, position 460.

Still further, compared with the BFD amino acid sequence, said BFD mutant protein can have or merely have any one or more of the following mutations: G25H, S26T, S26H, S26I, W86R, N87T, L109H, L109G, L110E, R184H, S236M, H281V, Q282F, N374D, N374E, S376V, T377G, T377M, T379R, T380C, T380Y, F397A, G401N, S430A, T457C, G459A, A460M.

More particularly, compared with the BFD amino acid sequence, said BFD mutant protein can have or merely have any one of the following mutations: W86R-N87T, W86R-N87T-L109G-L110E, W86R-N87T-L109G-L110E-T377M, W86R-N87T-L109G-L110E-A460M, W86R-N87T-L109G-L110E-H281V-Q282F-A460M, W86R-N87T-T377M-T380C, W86R-N87T-T377M-T380Y, N374D-S376V, S430A, T379R, S236M, W86R-N87T-R184H, G25H, N374D-T377G, T457C, S376V, S26T-G401N, N87T-T377G, S26H, S26I-N87T, F397A, N374E, N87T-G401N, N87T-R184H, L109H-G459A.

In the present invention, a following nomenclature is used for substitution of an amino acid: an original amino acid, a position, a substituted amino acid. For example, substitution of original tryptophan (W) at position 86 of the BFD amino acid sequence with arginine (R) is named as "W86R". A variant comprising multiple variations is separated by symbol "-".

More preferably, the BFD mutant protein provided by the present invention is shown by any one of 1)-4) as follows:

1) the amino acid sequence of the BFD mutant W86R-N87T as shown is a sequence obtained by mutating tryptophan at position 86 to arginine and asparaginate at position 87 to threonine and remaining other amino acid residues unvaried in the BFD amino acid sequence;

2) the BFD mutant W86R-N87T-L109G-L110E as shown is a sequence obtained by mutating tryptophan at position 86 to arginine, and asparaginate at position 87 to threonine, and leucine at 109 to glycine, and leucine at position 110 to glutamic acid and remaining other amino acid residues unvaried in the BFD amino acid sequence;

3) the BFD mutant W86R-N87T-L109G-L110E-A460M as shown is a sequence obtained by mutating tryptophan at position 86 to arginine, and asparaginate at position 87 to threonine, and leucine at position 109 to glycine, and leucine at position 110 to glutamic acid, and alanine at position 460 to methionine and remaining other amino acid residues unvaried in the BFD amino acid sequence;

4) the BFD mutant W86R-N87T-L109G-L110E-H281V-Q282F-A460M as shown is a sequence obtained by mutating tryptophan at position 86 to arginine, and asparaginate at position 87 to threonine, and leucine at position 109 to glycine, and leucine at position 110 to glutamic acid, and alanine at position 460 to methionine, and histidine at position 281 to valine, and glutamine at position 282 to phenylalanine and remaining other amino acid residues unvaried in the BFD amino acid sequence.

In the present invention, said BFD amino acid sequence particularly is SEQ ID No.1. Correspondingly, the BFD nucleotide sequence is SEQ ID No.2.

In third aspect, the present invention seeks to protect a DNA molecule capable of coding the above BFD mutant.

Compared with SEQ ID No.2, said DNA molecule is one that has or merely has base mutations at any one or more of the following positions: positions 73-75, positions 76-78, positions 256-258, positions 259-261, positions 325-327, positions 328-330, positions 550-552, positions 706-708, positions 841-843, positions 844-846, positions 1120-1122, positions 1126-1128, positions 1129-1131, positions 1135-1137, positions 1138-1140, positions 1189-1191, positions 1201-1203, positions 1288-1290, positions 1369-1371, positions 1375-1377, positions 1378-1380.

Further, compared with SEQ ID No.2, said DNA molecule is one that has or merely has any one or more of the following mutations: GGT 73-75 CAT, TCT 76-78 ACC, TCT 76-78 CAT, TCT 76-78 ATT, TGG 256-258 CGT, AAC 259-261 ACC, CTG 325-327 CAT, CTG 325-327 GGT, CTG 328-330 GAA, CGT 550-552 CAT, TCT 706-708 ATG, CAC 841-843 GTT, CAG 844-846 TTT, AAC 1120-1122 GAT, AAC 1120-1122 GAA, TCT 1126-1128 GTT, ACC 1129-1131 GGT, ACC 1129-1131 ATG, ACC 1135-1137 CGT, ACC 1138-1140 TGT, ACC 1138-1140 TAT, TTC 1189-1191 GCA, GGT 1201-1203 AAT, TCT 1288-1290 GCA, ACC 1369-1371 TGT, GGT 1375-1377 GCA, GCT 1378-1380 ATG.

Still further, compared with SEQ ID No.2, said DNA molecule is one that has or merely has any one of the following mutations: TGG 256-258 CGT/AAC 259-261

ACC, TGG256-258CGT/AAC 259-261 ACC/CTG 325-327 GGT/CTG 328-330 GAA, TGG 256-258 CGT/AAC 259-261 ACC/CTG 325-327 GGT/CTG 328-330 GAA/ACC 1129-1131 ATG, TGG 256-258 CGT/AAC 259-261 ACC/CTG 325-327 GGT/CTG 328-330 GAA/GCT 1378-1380 ATG, TGG 256-258 CGT/AAC 259-261 ACC/CTG 325-327 GGT/CTG 328-330 GAA/CAC 841-843 GTT/CAG 844-846 TTT/GCT 1378-1380 ATG, TGG 256-258 CGT/AAC 259-261 ACC/ACC 1129-1131 ATG/ACC 1138-1140 TGT, TGG 256-258 CGT/AAC 259-261 ACC/ACC 1129-1131 ATG/ACC 1138-1140 TAT, AAC 1120-1122 GAT/TCT 1126-1128 GTT, TCT 1288-1290 GCA, ACC 1135-1137 CGT, TCT 706-708 ATG, TGG 256-258 CGT/AAC 259-261 ACC/CGT 550-552 CAT, GGT 73-75 CAT, AAC 1120-1122 GAT/ACC 1129-1131 GGT, ACC 1369-1371 TGT, TCT 1126-1128 GTT, TCT 76-78 ACC/GGT 1201-1203 AAT, AAC 259-261 ACC/ACC 1129-1131 GGT, TCT 76-78 CAT, TCT 76-78 ATT/AAC 259-261 ACC, TTC 1189-1191 GCA, AAC 1120-1122 GAA, AAC 259-261 ACC/GGT 1201-1203 AAT, AAC 259-261 ACC/CGT 550-552 CAT, CTG 325-327 CAT/GGT 1375-1377 GCA.

In the present invention, a following nomenclature is used for substitution of a base: an original base, a position, a substituted base. Correspondingly, substitution of the original TGG at positions 256-258 of SEQ ID No.2 with CGT is named as "TGG256-258CGT". A variant comprising multiple variations is separated by symbol "/".

More preferably, said DNA molecule is shown by any one of 1)-4) as follows:

1) the DNA molecule as shown is a sequence (corresponding to W86R-N87T) obtained by mutating TGG at positions 256-258 to CGT and AAC at positions 259-261 to ACC and remaining other bases unvaried in SEQ ID No.2;

2) the DNA molecule as shown is a sequence (corresponding to W86R-N87T-L109G-L110E) obtained by mutating TGG at positions 256-258 to CGT, and AAC at positions 259-261 to ACC, and CTG at positions 325-327 to GGT, and CTG at positions 328-330 to GAA and remaining other bases unvaried in SEQ ID No.2;

3) the DNA molecule as shown is a sequence (corresponding to W86R-N87T-L109G-L110E-A460M) obtained by mutating TGG at positions 256-258 to CGT, and AAC at positions 259-261 to ACC, and CTG at positions 325-327 to GGT, and CTG at positions 328-330 to GAA, and GCT at positions 1378-1380 to ATG and remaining other bases unvaried in SEQ ID No.2;

4) the DNA molecule as shown is a sequence (corresponding to W86R-N87T-L109G-L110E-H281V-Q282F-A460M) obtained by mutating TGG at positions 256-258 to CGT, and AAC at positions 259-261 to ACC, and CTG at positions 325-327 to GGT, and CTG at positions 328-330 to GAA, and CAC at positions 841-843 to GTT, and CAG at positions 844-846 to TTT, and GCT at positions 1378-1380 to ATG and remaining other bases unvaried in SEQ ID No.2.

In fourth aspect, the present invention seeks to protect a recombinant vector, an expression cassette, a transgenic cell line or recombinant bacteria comprising the above DNA molecule.

In fifth aspect, the present invention seeks to protect use of the above BFD mutant protein, the above DNA molecule or the above recombinant vector, the expression cassette, the transgenic cell line or the recombinant bacteria in the following applications:

use of the above BFD mutant protein, the above DNA molecule or the above recombinant vector, the expression cassette, the transgenic cell line or the recombinant bacteria in catalyzing formaldehyde to be condensed to hydroxyl acetaldehyde and/or 1,3-dihydroxyacetone;

or use of the above BFD mutant protein, the above DNA molecule or the above recombinant vector, the expression cassette, the transgenic cell line or the recombinant bacteria in preparing a product for catalyzing formaldehyde to be condensed to hydroxyl acetaldehyde and/or 1,3-dihydroxyacetone;

or use of the above BFD mutant protein, the above DNA molecule or the above recombinant vector, the expression cassette, the transgenic cell line or the recombinant bacteria in catalyzing formaldehyde to generate acetyl coenzyme A or acetyl phosphoric acid;

or use of the above BFD mutant protein, the above DNA molecule or the above recombinant vector, the expression cassette, the transgenic cell line or the recombinant bacteria in preparing a product for catalyzing formaldehyde to generate acetyl coenzyme A or acetyl phosphoric acid.

In sixth aspect, the present invention seeks to protect the following applications:

use of the above BFD mutant protein and the F/XPK protein in catalyzing formaldehyde to generate acetyl phosphoric acid;

or use of the above BFD mutant protein and the F/XPK protein in preparing a product for catalyzing formaldehyde to generate acetyl phosphoric acid;

or use of the above BFD mutant protein, the F/XPK protein and the phosphotransacetylase in catalyzing formaldehyde to generate acetyl coenzyme A;

or use of the above BFD mutant protein, the F/XPK protein and the phosphotransacetylase in preparing a product for catalyzing formaldehyde to generate acetyl coenzyme A.

In the present invention, the amino acid sequence of said F/XPK protein particularly is SEQ ID No.3, and its corresponding coding gene sequence particularly is SEQ ID No.4. The amino acid sequence of said phosphotransacetylase particularly is SEQ ID No.5, and its corresponding coding gene sequence particularly is SEQ ID No.6.

In seventh aspect, the present invention seeks to protect any one of the following products:

(1) a product for catalyzing formaldehyde to be condensed to hydroxyl acetaldehyde and/or 1,3-dihydroxyacetone comprising the above BFD mutant protein.

(2) a product for catalyzing formaldehyde to generate acetyl phosphoric acid comprising the above BFD mutant protein and F/XPK protein.

(3) a product for catalyzing formaldehyde to generate acetyl coenzyme A comprising the above BFD mutant protein, F/XPK protein and phosphotransacetylase.

In the present invention, the amino acid sequence of said F/XPK protein particularly is SEQ ID No.3, and its corresponding coding gene sequence particularly is SEQ ID No.4. The amino acid sequence of said phosphotransacetylase particularly is SEQ ID No.5, and its corresponding coding gene sequence particularly is SEQ ID No.6.

BRIEF DESCRIPTION OF THE DRAWINGS

FIG. 1 is a plasmid map of pET-28a-BFD and pET-28a-F/XPK.

FIG. 2 is the GC-MS detection of hydroxyl acetaldehyde.

FIG. 3 is the GC-MS detection of 1,3-dihydroxyacetone.

FIG. 4 is the catalyzing of hydroxyl acetaldehyde or 1,3-dihydroxyacetone by the F/XPK protein to obtain acetyl phosphoric acid.

DETAILED DESCRIPTION

The following examples facilitate a better understanding of the present invention, but without limitation of the present invention. The experimental methods in the following examples are all conventional methods, unless specifically indicated. The experimental materials in the following examples are all available from a shop selling conventional biochemical reagents, unless specifically indicated. The quantitative tests in the following examples are all repeated in triplicate, the results of which are averaged.

Example 1. Construction of an Expression Vector

1. Construction of a Vector Expressing a BFD Mutant

The genus of the coding gene of a BFD enzyme is sourced from *Pseudomonas putida*. The amino acids of the BFD enzyme are shown as SEQ ID No.1, and the nucleotide sequence of the coding gene of the BFD enzyme is shown as SEQ ID No.2. A vector expressing the BFD enzyme is one obtained by inserting the coding gene (SEQ ID No.2) of the above BFD enzyme between the enzymatic cleavage sites of NdeI and XhoI in a pET-28a vector, and is named as pET-28a-BFD (as shown by A in FIG. 1)

Each of vectors expressing a BFD mutant is one obtained by inserting a coding gene (see Table 1) of different BFD mutants between the enzymatic cleavage sites of NdeI and XhoI in a pET-28a vector.

2. Construction of a Vector Expressing F/XPK

The genus of a F/XPK gene is sourced from *Bifidobacterium adolescentis*. The amino acids of the F/XPK protein are shown as SEQ ID No.3, and the nucleotide sequence of the coding gene of the F/XPK protein is SEQ ID No.4.

Figure 1:
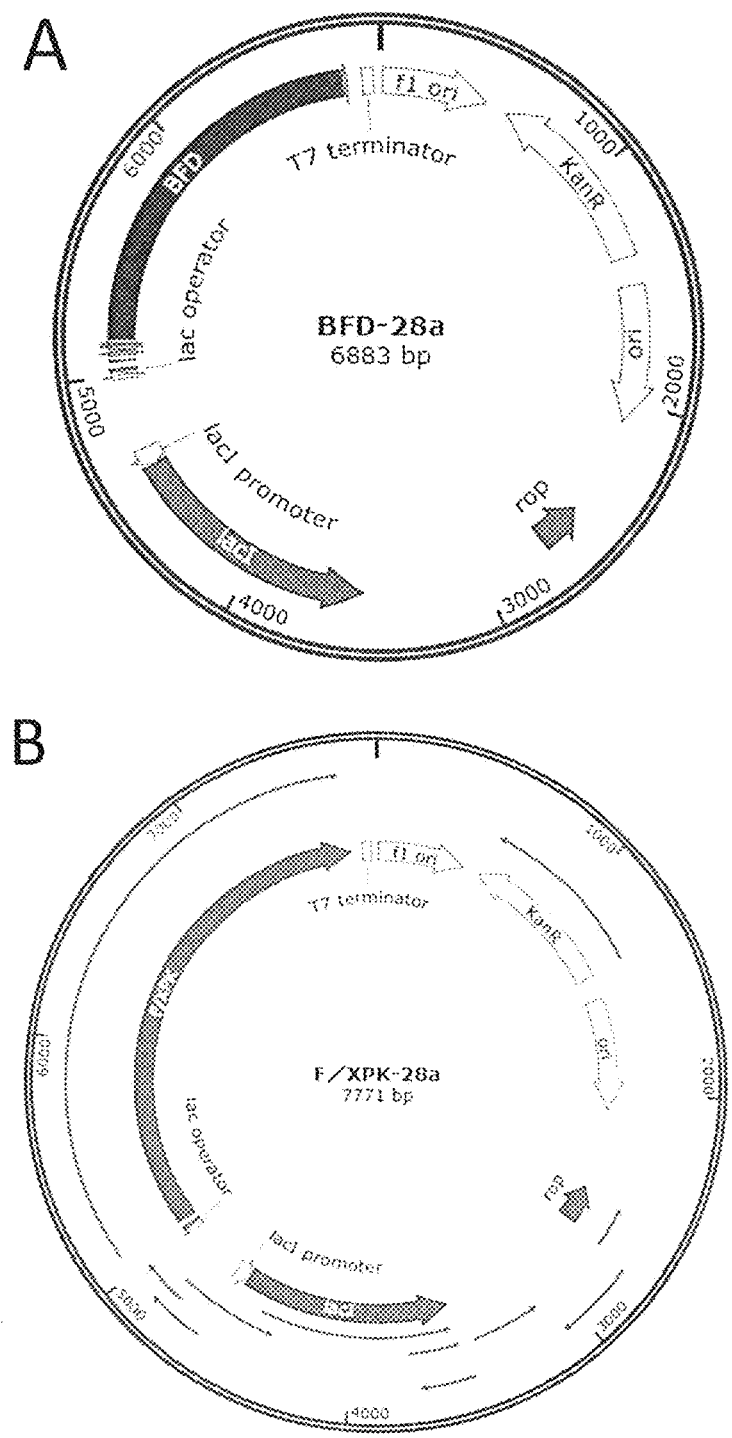
Figure 1:
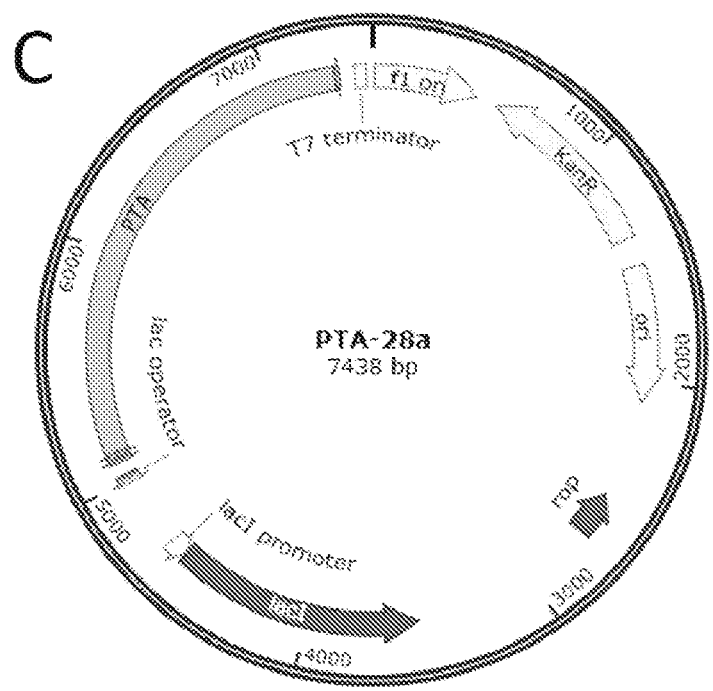

A vector expressing F/XPK is one obtained by inserting the coding gene (SEQ ID No.4) of the above F/XPK protein between the enzymatic cleavage sites of NdeI and XhoI in a pET-28a vector, and is named as pET-28a-F/XPK (as shown by B in FIG. 1).

3. Construction of a Vector Expressing PTA

The genus of a PTA gene is sourced from *Escherichia coli*. The amino acids of the PTA protein are shown as SEQ ID No.5, and the nucleotide sequence of the coding gene of the PTA protein is SEQ ID No.6.

A vector expressing PTA is one obtained by inserting the coding gene (SEQ ID No.6) of the above PTA protein between the enzymatic cleavage sites of NdeI and XhoI in a pET-28a vector, and is named as pET-28a-PTA (as shown by C in FIG. 1).

Example 2. Expression of a Protein

In order to in vitro detect the activity of a BFD wild-type and a mutant, F/XPK, and a PTA enzymes, an exogenous expression and a purification of the enzymes are performed in *E. coli*.

(1) The *E. coli* expressing recombinant plasmid pET-28a-BFD, each of vectors expressing the BFD mutant, the pET-28a-F/XPK, and the pET-28a-PTA prepared in the above II are respectively transformed into *E. coli* BL21 (DE3) to obtain recombinant bacteria expressing the BFD enzyme, each of recombinant bacteria expressing the BFD mutant, recombinant bacteria expressing F/XPK and recombinant bacteria expressing PTA. Positive clones are screened by using a kanamycin-resistant plate (Kan+, 100 mg/mL), followed by overnight culture at 37° C.;

(2) A monoclone is streaked into a 5 mL LB liquid medium (Kan+, 100 mg/mL), followed by culture at 37° C., 220 r/min until $OD_{600}$ reaches 0.6-0.8. The bacteria liquid in the 5 mL LB medium is transferred to a 800 mL 2YT medium (Kan+, 100 mg/mL), followed by culture at 37° C., 220 rpm until $OD_{600}$ reaches 0.6-0.8, then the temperature is cooled to 16° C. and IPTG is added to a final concentration of 0.5 mM, followed by induction expression for 16 h;

(3) The above cultured bacteria liquid is collected in a bacteria collecting bottle, followed by centrifugation for 15 min at 5500 rpm;

(4) Supernatants are abandoned. The obtained bacteria precipitates are suspended in a 35 mL protein buffer (50 mM phosphate buffer, pH7.4) and poured into a 50 mL centrifuge tube, and then kept in a refrigerator at −80° C. Bacteria expressing the BFD enzyme, each of bacteria expressing the BFD mutant, bacteria expressing F/XPK and bacteria expressing PTA are obtained.

Example 3. Purification of a Protein (1) Disruption of bacteria: bacteria expressing the BFD enzyme, each of bacteria expressing the BFD mutant, bacteria expressing F/XPK and bacteria expressing PTA are respectively disrupted twice using a high pressure and low temperature disruptor at the pressure of 1200 bar, at 4° C. Centrifugation for 45 min at 4° C., 10000 rpm is performed;

(2) Purification: suction filtration of supernatants through a 0.45 μm micropore filter membrane is performed, followed by Ni affinity chromatography purification, and the steps are detailed as follows.

a: Column balance: the Ni affinity chromatography column is first washed by $ddH_2O$ with 2 column volumes, and then is balanced by a protein buffer with 1 column volume, before supernatants are loaded;

b: Loading: the supernatants are slowly passed through the Ni affinity chromatography column in a flow rate of 0.5 mL/min, which is repeated once;

c: Elution of impure proteins: a protein buffer is used for washing with 1 column volume, and then an elution of strongly binded impure proteins with 50 mL of a protein buffer containing 50 mM, 100 mM imidazole is performed respectively;

d: Elution of a target protein: an elution of a target protein with 20 mL of a protein buffer (50 mM potassium phosphate, PH=7.4, 5 mM $MgSO_4$) containing 200 mM imidazole is performed. The first several drops of flow-through samples are taken for making a sample, followed by a detection with 12% SDS-PAGE.

(3) Liquid change: the collected target protein is concentrated to 1 mL in a 50 mL Amicon ultrafiltration tube (30 kDa, Millipore company) by centrifugation (4° C., 3400 r/min). 15 mL of a protein buffer free of imidazole is added and then concentrated to 1 mL, which is repeated once. BFD, F/XPK, and PTA proteins are obtained, respectively.

(4) the concentration of the protein after concentration is detected by an Nondrop 2000 micro-spectrophotometer and diluted to 10 mg/mL, that is, a BFD protein, each of BFD mutant proteins, a F/XPK protein and a PTA protein are obtained.

Example 4. Detection of the Function of a BFD Wild-Type and a Mutant Protein

1. A BFD Wild-Type Protein Catalyzes Formaldehyde to be Condensed to Hydroxyl Acetaldehyde Sample: 1 mg/mL BFD, 50 mM potassium phosphate buffer, 5 mM $MgCl_2$, 0.5 mM thiamine pyrophosphate (TPP), at pH 7.5, and 2 g/L formaldehyde.

Control: 50 mM potassium phosphate buffer, 5 mM MgCl$_2$, 0.5 mM TPP, at pH 7.5, and 2 g/L formaldehyde.

Standard: 0.1 g/L hydroxyl acetaldehyde.

The reaction system is placed at 37° C. for reaction for 1 h after being uniformly mixed. The reaction system is lyophilized after the reaction is finished. Then 60 µL of pentafluorobenzene hydroxylamine hydrochloride (PFBOA, 200 mM) is added and whirled, followed by incubation for 1 h at room temperature. 300 µL of hexane is added and placed at room temperature for 5 min. 100 µL of the sample in the organic layer is taken, into which 30 µL of trimethylsilicyl trifluoroacetamide containing 1% trimethylchlorosilane and 20 µL of proline are added to silylanize the PFBOA derivative. The sample is detected by GC-MS.

GC-MS detection: the detection system is an Agilent Gas Chromatography 7890A; detection conditions are: Agilent chromatographic column 19091S-433, 30 m×250 µm×0.25 µm; starting temperature is set to be 50° C., with retention time of 1 min, the temperature is increased to 150° C. in a linear increasing rate of 15° C./min, and then to 300° C. in 30° C./min, with retention time of 1 min; the injection port temperature is 250° C., the GC-MS interface temperature is 280° C. Helium gas is for a carrying gas with a flow rate of 1.2 mL/min. Injection volume is 1 µL, and the solvent delay for 5 min is detected.

Figure 2:
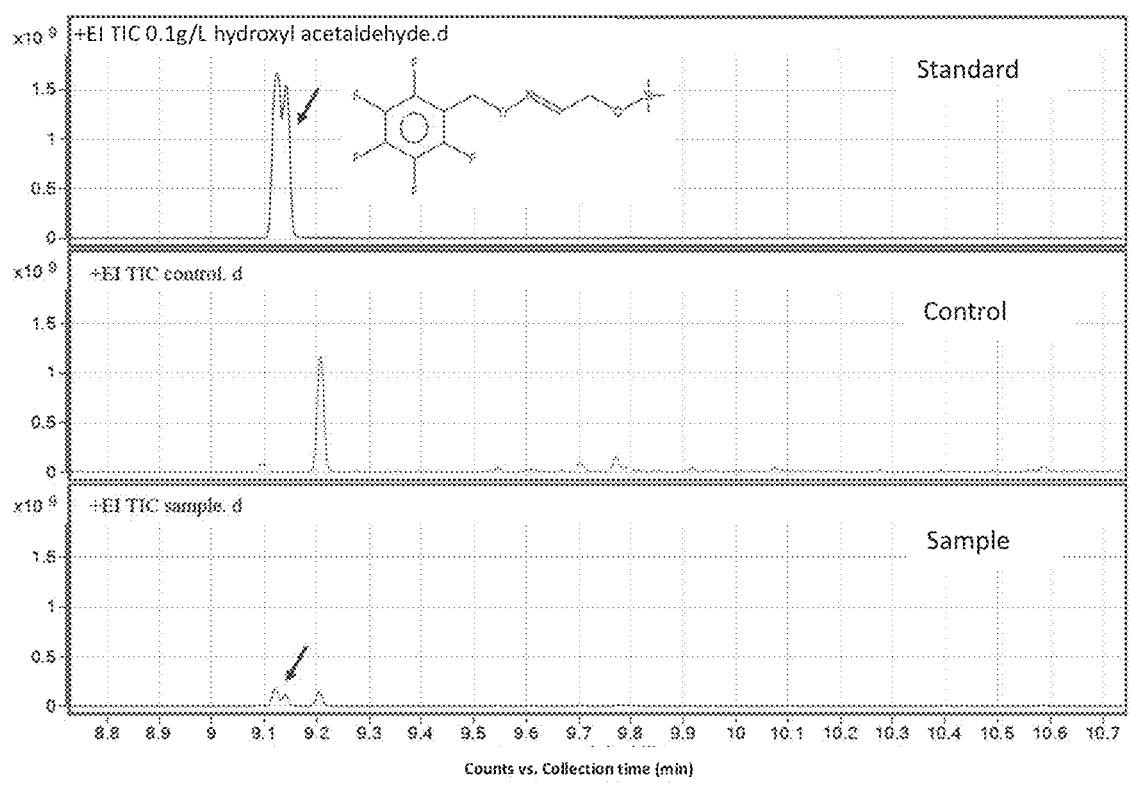

As can be known from the GC-MS analysis, BFD can catalyze formaldehyde to generate hydroxyl acetaldehyde, and the results are shown in FIG. 2.

2. A BFD Wild-Type Protein Catalyzes Formaldehyde to be Condensed to 1,3-Dihydroxyacetone Sample: 1 mg/mL BFD, 50 mM potassium phosphate buffer, 5 mM MgCl$_2$, 0.5 mM TPP, at pH 7.5, and 2 g/L formaldehyde.

Control: 50 mM potassium phosphate buffer, 5 mM MgCl$_2$, 0.5 mM TPP, at pH 7.5, and 2 g/L formaldehyde.

Standard: 0.1 g/L 1,3-dihydroxyacetone.

The reaction system is placed at 37° C. for reaction for 1 h after being uniformly mixed. The reaction system is lyophilized after the reaction is finished. Then trimethylsilicyl trifluoroacetamide (60 µL) containing 1% trimethylchlorosilane and pyridine (200 µL) are added and whirled at 60° C. for 10 min. The sample is detected by GC-MS.

GC-MS detection:

Injection volume: 1 µL; injecting without splitting stream;

Injection port temperature: 250° C.

Chromatographic column: J&W HP-5 (30 m×250 µm×0.25 µm)

Figure 3:
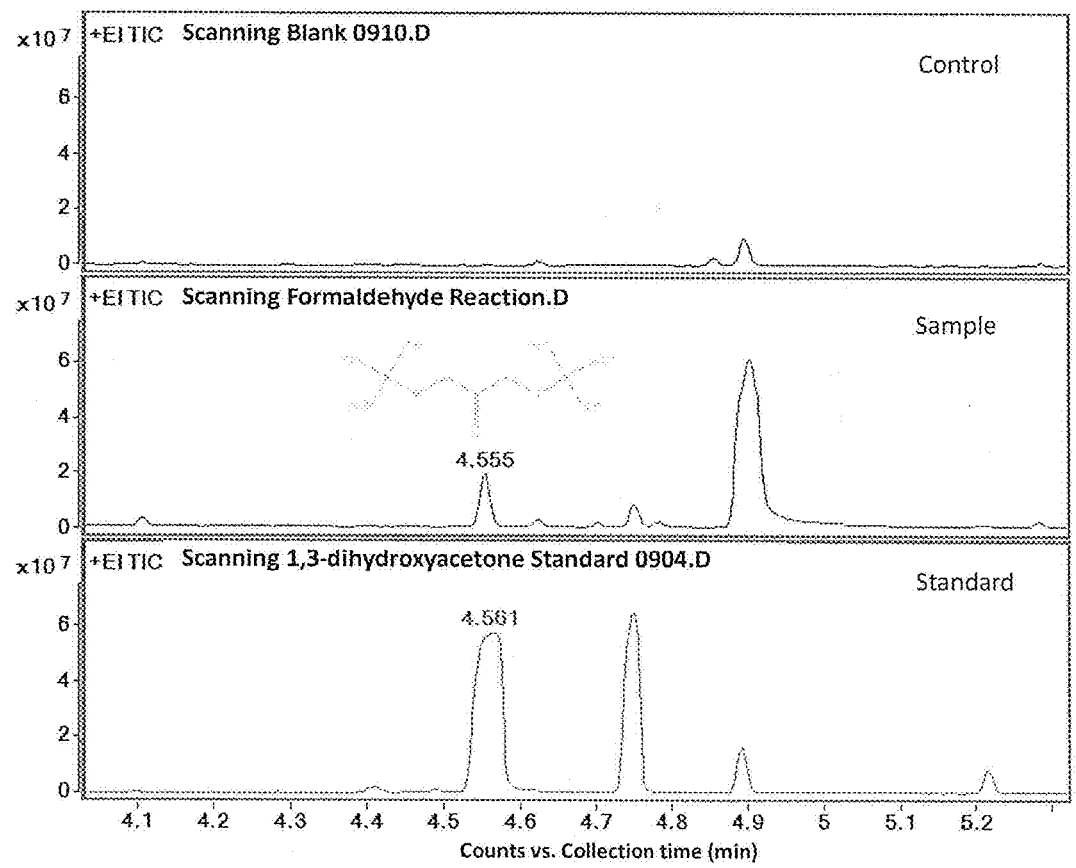

Column box temperature: keeping at 80° C. for 1 min, and increasing to 280° C. in 20° C./min; increasing to 310° C. in 10° C./min and keeping for 6 min GC/MS interface temperature: 280° C.
EI ion source temperature: 230° C.
Ionization energy: 70 eV
Solvent delay: 2.5 min
Scanning range: 50-500 amu
Collecting rate: 5 spectra/s As can be known from the GC-MS analysis, BFD can catalyze formaldehyde to generate 1,3-dihydroxyacetone, and the results are shown in FIG. 3.

3. Whole Cells of a BFD Wild-Type and Mutant Catalyze Formaldehyde to be Condensed to Hydroxyl Acetaldehyde and 1,3-Dihydroxyacetone The recombinant bacteria expressing the BFD wild-type and each of those expressing BFD mutants prepared in Example 2 are respectively cultured in 200 mL 2YT at 37° C. until OD$_{600}$=0.6, followed by induction with 0.5 mM IPTG at 16° C. for 18 h, and centrifugation for 15 min at 3500 rpm. A protein buffer (50 mM potassium phosphate buffer, 5 mM MgCl$_2$, 0.5 mM TPP, at pH 7.5) is used for washing off the medium, and the bacteria are collected. Then, 20 mL of a protein buffer added with 0.5 mM TPP is used for respective resuspension. 500 µL of the resuspended bacteria liquid is taken, into which 500 µL of a formaldehyde solution with a final concentration of 5 g/L containing 0.5 mM TPP formulated by a protein buffer is then added, followed by reacting for 2 h at 37° C., 750 rpm, and centrifugation such that supernatants are taken for detection by liquid chromatography.

The detection by liquid chromatography uses an AMINEX HPX-87H, 300×7.8MM column. The mobile phase is 5 mM sulfuric acid. 20 µL is injected each time. The column box temperature is 35° C. Hydroxyl acetaldehyde and 1,3-dihydroxyacetone are detected at 200 nm under ultraviolet conditions, and an external standard method is used to determine the content.

The results are shown in Table 1. As can be seen, compared with a BFD without mutation, all the yields of 1,3-dihydroxyacetone condensed by catalyzing formaldehyde with BFD mutant proteins are increased;

Compared with a BFD without mutation, the yield of hydroxyl acetaldehyde from W86R-N87T is the highest among BFD mutants having double mutations; the yield of hydroxyl acetaldehyde from W86R-N87T-L109G-L110E is the highest among BFD mutants having four mutations; the yield of hydroxyl acetaldehyde from W86R-N87T-L109G-L110E-A460M is the highest among BFD mutants having five mutations; the yield of hydroxyl acetaldehyde from W86R-N87T-L109G-L110E-H281V-Q282F-A460M is the highest among BFD mutants having seven mutations; and they are higher than those from other mutation sites.

TABLE 1 shows detection of the activity of a BFD mutant

| BFD mutant | | substitution | hydroxyl acetaldehyde g/L | 1,3-dihydroxyacetone g/L |
|---|---|---|---|---|
| BFD wild-type | protein | SEQ ID No. 1 | 0.00972 | 0.00882 |
| | gene | SEQ ID No. 2 | | |
| M1 | protein | N374D-S376V | 0.00972 | 0.01242 |
| | gene | AAC 1120-1122 GAT/TCT 1126-1128 GTT | | |
| M2 | protein | S430A | 0.01116 | 0.00246 |
| | gene | TCT 1288-1290 GCA | | |
| M3 | protein | T379R | 0.01116 | 0.0117 |
| | gene | ACC 1135-1137 CGT | | |
| M4 | protein | S236M | 0.01224 | 0.00192 |
| | gene | TCT 706-708 ATG | | |

TABLE 1-continued shows detection of the activity of a BFD mutant

| BFD mutant | | substitution | hydroxyl acetaldehyde g/L | 1,3-dihydroxyacetone g/L |
|---|---|---|---|---|
| M5 | protein | W86R-N87T-R184H | 0.0126 | 0.00954 |
| | gene | TGG 256-258 CGT/AAC 259-261 ACC/CGT 550-552 CAT | | |
| M6 | protein | G25H | 0.01368 | 0.0096 |
| | gene | GGT 73-75 CAT | | |
| M7 | protein | N374D-T377G | 0.01584 | 0.0048 |
| | gene | AAC 1120-1122 GAT/ACC 1129-1131 GGT | | |
| M8 | protein | T457C | 0.018 | 0.0024 |
| | gene | ACC 1369-1371 TGT | | |
| M9 | protein | S376V | 0.01944 | 0.00822 |
| | gene | TCT 1126-1128 GTT | | |
| M10 | protein | S26T-G401N | 0.02304 | 0.04404 |
| | gene | TCT 76-78 ACC/GGT 1201-1203 AAT | | |
| M11 | protein | N87T-T377G | 0.02592 | 0.00816 |
| | gene | AAC 259-261 ACC/ACC 1129-1131 GGT | | |
| M12 | protein | S26H | 0.02736 | 0.00942 |
| | gene | TCT 76-78 CAT | | |
| M13 | protein | S261-N87T | 0.03024 | 0.00852 |
| | gene | TCT 76-78 ATT/AAC 259-261 ACC | | |
| M14 | protein | F397A | 0.0306 | 0.009 |
| | gene | TTC 1189-1191 GCA | | |
| M15 | protein | N374E | 0.03096 | 0.01266 |
| | gene | AAC 1120-1122 GAA | | |
| M16 | protein | N87T-G401N | 0.0378 | 0.00798 |
| | gene | AAC 259-261 ACC/GGT 1201-1203 AAT | | |
| M17 | protein | N87T-R184H | 0.0378 | 0.00882 |
| | gene | AAC 259-261 ACC/CGT 550-552 CAT | | |
| M18 | protein | L109H-G459A | 0.06084 | 0.01062 |
| | gene | CTG 325-327 CAT/GGT 1375-1377 GCA | | |
| M19 | protein | W86R-N87T | 0.08064 | 0.01086 |
| | gene | TGG 256-258 CGT/AAC 259-261 ACC | | |
| M20 | protein | W86R-N87T-T377M-T380C | 0.56052 | 0.09468 |
| | gene | TGG 256-258 CGT/AAC 259-261 ACC/ACC 1129-1131 ATG/ACC 1138-1140 TGT | | |
| M21 | protein | W86R-N87T-T377M-T380Y | 0.56268 | 0.05058 |
| | gene | TGG 256-258 CGT/AAC 259-261 ACC/ACC 1129-1131 ATG/ACC 1138-1140 TAT | | |
| M22 | protein | W86R-N87T-L109G-L110E | 0.57312 | 0.0189 |
| | gene | TGG 256-258 CGT/AAC 259-261 ACC/CTG 325-327 GGT/CTG 328-330 GAA | | |
| M23 | protein | W86R-N87T-L109G-L110E-T377M | 0.57564 | 0.08562 |
| | gene | TGG 256-258 CGT/AAC 259-261 ACC/CTG 325-327 GGT/CTG 328-330 GAA/ACC 1129-1131 ATG | | |
| M24 | protein | W86R-N87T-L109G-L110E-A460M | 0.756 | 0.27 |
| | gene | TGG 256-258 CGT/AAC 259-261 ACC/CTG 325-327 GGT/CTG 328-330 GAA/GCT 1378-1380 ATG | | |
| M25 | protein | W86R-N87T-L109G-L110E-H281V-Q282F-A460M | 1.4357 | 0.221 |
| | gene | TGG 256-258 CGT/AAC 259-261 ACC/CTG 325-327 GGT/CTG 328-330 GAA/CAC 841-843 GTT/CAG 844-846 TTT/GCT 1378-1380 ATG | | |

Notes: the numbering of a protein substitution is started from the N-terminal of the amino acid sequence shown by SEQ ID No.1; the numbering of a gene substitution is started from the 5'end of the nucleotide sequence shown by SEQ ID No.2. In the table, a following nomenclature is used for substitution of an amino acid: an original amino acid, a position (that is, the position in SEQ ID No.1), a substituted amino acid. Correspondingly, substitution of the original tryptophan at position 86 of SEQ ID No.1 with arginine is named as "W86R". A following nomenclature is used for substitution of a base substitution: an original base, a position (that is, the positions in SEQ ID No.2), a substituted base. Correspondingly, substitution of the original TGG at positions 256-258 of SEQ ID No.2 with CGT is named as "TGG256-258CGT". A variant in a protein comprising multiple variations is separated by symbol "-"; a variant in a gene comprising multiple variations are separated by symbol "/".

Example 5. Catalyzing of Hydroxyl Acetaldehyde or 1,3-Dihydroxyacetone by a F/XPK Protein to Obtain Acetyl Phosphoric Acid 1. Formulation of Detection Reagents:

2M hydroxylamine hydrochloride (100 mL) at pH 7.5: 13.5 g of solid hydroxylamine hydrochloride is weighed and dissolved in 190 mL of ddH$_2$O, the pH of which is adjusted to 6.5 with solid sodium hydroxide, followed by performing a constant volume to 200 mL with ddH$_2$O.

Developer 1: 15% trichloroacetic acid (10 mL); 150 mg of trichloroacetic acid is weighed and dissolved in 10 mL of ddH$_2$O.

Developer 2: 4M HCl (10 mL); 3.333 mL of concentrated hydrochloric acid is taken and dissolved in dd$H_2O$, followed by performing a constant volume to 10 mL.

Developer 3: 5% ferric trichloride (10 mL); 50 mg of ferric trichloride is weighed and dissolved in 0.1M HCl, followed by performing a constant volume to 10 mL.

2. Reaction

1) Catalyzing of hydroxyl acetaldehyde or 1,3-dihydroxyacetone with F/XPK:

Experimental group: 10 mM 1,3-dihydroxyacetone or hydroxyl acetaldehyde, 50 mM potassium phosphate buffer, 5 mM $MgCl_2$, 0.5 mM TPP, at pH 7.5, 2 mg/mL F/XPK; after shaking reaction for 2 h at 37° C., a reaction liquid is obtained.

Enzyme-free control: 10 mM 1,3-dihydroxyacetone or hydroxyl acetaldehyde, 50 mM potassium phosphate buffer, 5 mM $MgCl_2$, 0.5 mM TPP, at pH 7.5; after shaking reaction for 2 h at 37° C., a reaction liquid is obtained.

Substrate-free control: 50 mM potassium phosphate buffer, 5 mM $MgCl_2$, 0.5 mM TPP, at pH 7.5, 2 mg/mL F/XPK; after shaking reaction for 2 h at 37° C., a reaction liquid is obtained.

Detection method: 75 μL of the above reaction liquid is taken to react with 75 μL of 2M hydroxylamine hydrochloride solution at pH 7.5 for 10 min at 30° C. Then 50 μL of each of developer 1, developer 2, and developer 3 are added. The reaction liquid after development is centrifuged for 2 min at 12000 rpm, and 130 μL of supernatant is taken to measure its (acetyl phosphoric acid) absorbance at 505 nm.

Figure 4:
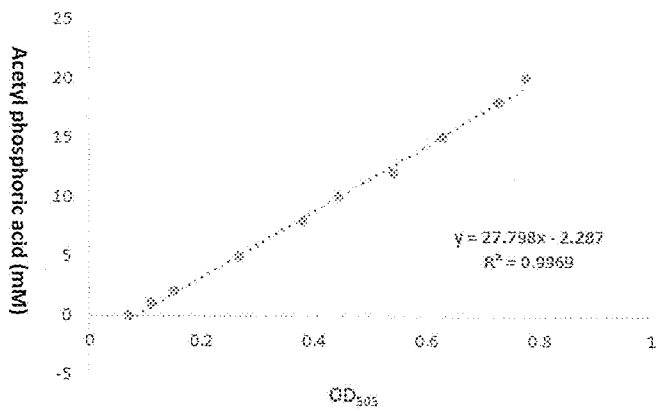
Figure 4:
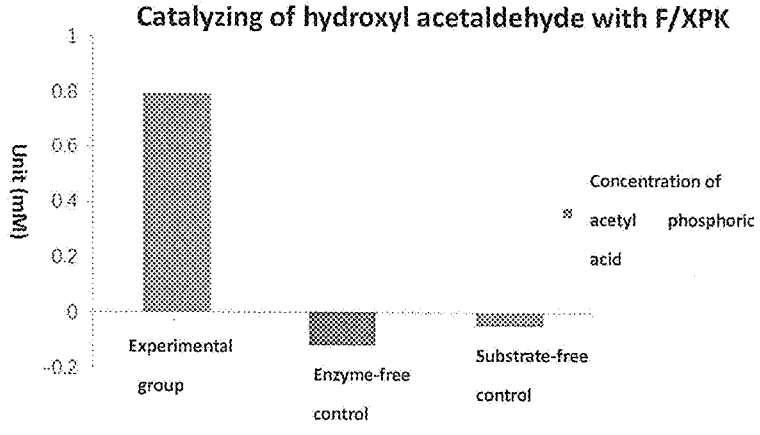
Figure 4:
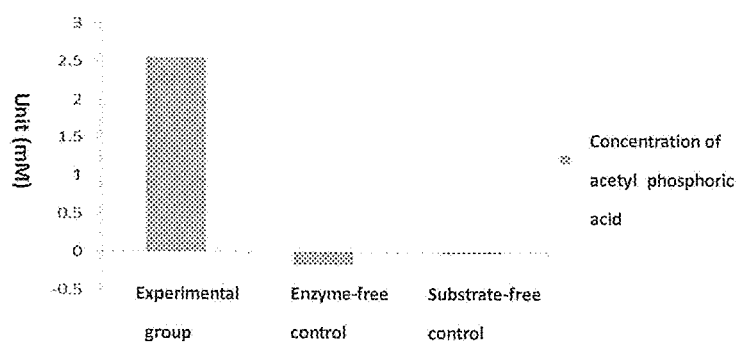

The results are seen in FIG. 4. As can be seen, hydroxyl acetaldehyde or 1,3-dihydroxyacetone can generate acetyl phosphoric acid, which is catalyzed by a F/XPK protein.

Example 6. Synthesis of Acetyl Coenzyme A with Catalyzing of Acetyl Phosphoric Acid by a PTA Enzyme 1. Generation of Acetyl Coenzyme A with Catalyzing of Acetyl Phosphoric Acid by PTA 1 mg/ml PTA, 3 mM acetyl phosphoric acid, 2 mM CoA, 50 mM potassium phosphate buffer, 5 mM $MgCl_2$, 0.5 mM TPP, at pH 7.5; after shaking reaction for 0 min and 10 min at 37° C., reaction liquids are obtained.

Detection method: 1 mL of the reaction liquid is taken to measure its absorbance at 233 nm, and the results are seen in Table 2.

Table 2 Shows Detection Data for the Synthesis of Acetyl Coenzyme A by Acetyl Phosphoric Acid

| Reaction time | $OD_{233}$ |
| --- | --- |
| 0 min | 0.640 |
| 10 min | 1.077 |

Calculation Method:

$OD_{233}$ for the reaction for 0 min is taken as $E_1$, and $OD_{233}$ for the reaction for 10 min is taken as $E_2$. The difference of the molar extinction coefficients between acetyl coenzyme A and CoA is $\Delta\varepsilon$.

$C_{acetyl\ coenzyme\ A}$ is the concentration of acetyl coenzyme A $$C_{acetyl\ coenzyme\ A} = 10*(E_2-E_1)/\Delta\varepsilon$$

The concentration of acetyl coenzyme A is 0.98 mM.

Example 7. Double-Enzyme Catalyzing of Formaldehyde with a BFD Mutant and a F/XPK to Obtain Acetyl Phosphoric Acid Experimental group: 2 g/L formaldehyde, 50 mM potassium phosphate buffer, 5 mM $MgCl_2$, 0.5 mM TPP, at pH7.5, 1 mg/mL BFD or its mutant, 2 mg/mL F/XPK; after shaking reaction for 2 h at 37° C., a reaction liquid is obtained.

Enzyme-free control: 2 g/L formaldehyde, 50 mM potassium phosphate buffer, 5 mM $MgCl_2$, 0.5 mM TPP, at pH7.5; after shaking reaction for 2 h at 37° C., a reaction liquid is obtained.

Substrate-free control: 50 mM potassium phosphate buffer, 5 mM $MgCl_2$, 0.5 mM TPP, at pH7.5, 1 mg/mL BFD or its mutant, 2 mg/mL F/XPK; after shaking reaction for 2 h at 37° C., a reaction liquid is obtained.

Detection method: 75 μL of the above reaction liquid is taken to react with 75 μL of 2M pH7.5 hydroxylamine hydrochloride solution for 10 min at 30° C. After that, 50 μL of each of developer 1, developer 2, and developer 3 is added. The reaction liquid after development is centrifuged at 12000 rpm for 2 min, and 130 μL of the supernatant is taken to measure its (acetyl phosphoric acid) absorbance at 505 nm.

Figure 5:
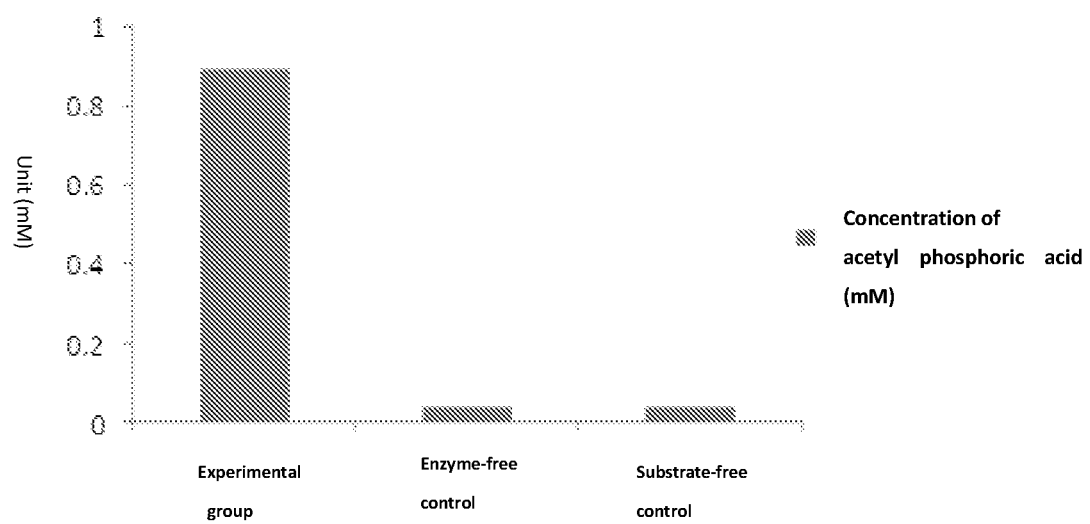
FIG. 5 is the double-enzyme catalyzing of formaldehyde by the BFD mutant and the F/XPK to obtain acetyl phosphoric acid.

The result of BFD mutant W86R-N87T-L109G-L110E-H281V-Q282F-A460M is shown in FIG. 5. As can be seen, the above BFD mutant protein along with F/XPK protein catalyzes formaldehyde to obtain acetyl phosphoric acid.

Example 8. Three-Enzyme Catalyzing of Formaldehyde with a BFD Mutant W86R-N87T-L109G-L110E-H281V-Q282F-A460M, F/XPK and PTA to Generate Acetyl Coenzyme A 0.2 mg/ml BFD mutant W86R-N87T-L109G-L110E-H281V-Q282F-A460M, 0.2 mg/ml F/XPK, 0.2 mg/ml PTA, 0.1 g/L formaldehyde, 10 mM potassium phosphate, 2 mM CoA, 50 mM potassium phosphate buffer, 5 mM $MgCl_2$ and 0.5 mM TPP, at pH7.5, are subjected to the shaking reaction for 2 h at 37° C. to obtain a reaction liquid.

Detection method I: 1 mL of the reaction liquid is taken to measure its absorbance at 233 nm. The results are seen in Table 3.

Table 3 Shows Detection Data for the Synthesis of Acetyl Coenzyme A by Formaldehyde

| Reaction time | $OD_{233}$ |
| --- | --- |
| 0 min | 0.033 |
| 120 min | 0.147 |

Calculation Method:

$OD_{233}$ for the reaction for 0 min is taken as Ea, and $OD_{233}$ for the reaction for 120 min is taken as Eb. The difference of the molar extinction coefficients between acetyl coenzyme A and CoA is $\Delta\varepsilon$. $C_{acetyl\ coenzyme\ A}$ is the concentration of acetyl coenzyme A.

$$C_{acetyl\ coenzyme\ A} = 10*(Eb-Ea)/\Delta\varepsilon$$

As can be seen, the concentration of acetyl coenzyme A obtained by using formaldehyde as a substrate is 0.257 mM.

The catalyzing of 0.1 g/L formaldehyde by a wild-type BFD obtains no hydroxyl acetaldehyde and 1,3-dihydroxyacetone, thus, no acetyl coenzyme A is detected by a reaction of a wild-type BFD with the other two enzymes.

Detection method II: 100 μL of the reaction liquid is taken to be added with 300 μL of acetonitrile for LC-MS detection.

LC Conditions:

Instrument: Shimadzu LC-30A; chromatographic column: Merck zic-HILIC (100 mm×2.1 mm, 3.5 μm); mobile phase A is 10 mM ammonium acetate, and mobile phase B is 100% acetonitrile. Condition for a gradient liquid chromatography is: 0-3 min, 90% B; 3-25 min, 90%-60% B; 25-30 min, 60% B; 30-38 min, 90% B; flow rate: 0.3 mL/min.

MS Conditions:

Instrument: ABSciex TripleTOF5600; ESI source; positive ion detection mode; voltage 5500V; ion source temperature 600° C.; GS1 gas pressure: 55 psi; GS2 gas pressure: 55 psi; curtain gas pressure: 35 psi; IDA collection mode, primary scanning range 50-1200 Da, secondary scanning range 30-1200 Da.

Figure 6:
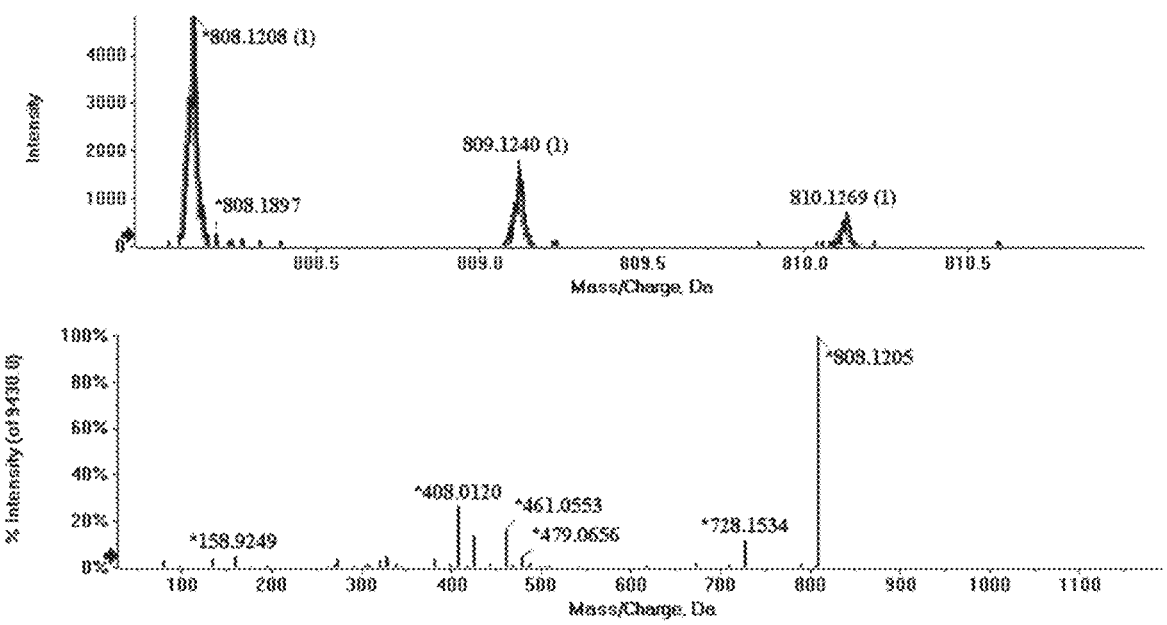
FIG. 6 is the LC-MS detection of acetyl coenzyme A.

The results are seen in FIG. 6. As can be seen, formaldehyde can be catalyzed to acetyl coenzyme A with three enzymes: a BFD mutant, F/XPK and PTA.

Example 9. To Obtain Biosynthesis Pathways of Acetyl Coenzyme A with Formaldehyde As can be seen from above, biosynthesis pathways of acetyl coenzyme A with formaldehyde can be any one of the following pathways:

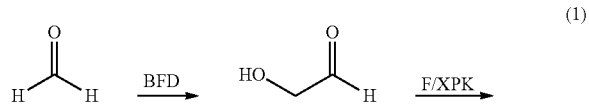

(1)

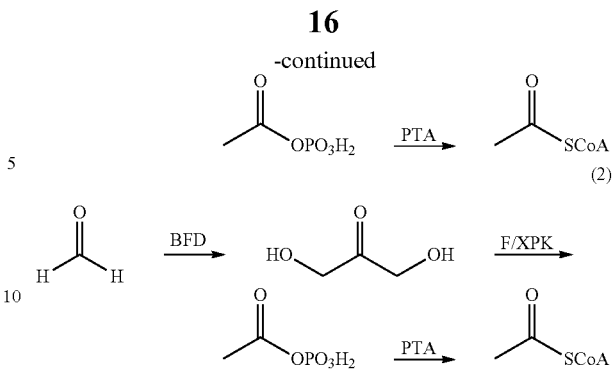

(2)

The experiments of the present invention demonstrate that there does not exist an enzyme in the nature for catalyzing formaldehyde to be condensed to hydroxyl acetaldehyde or 1,3-dihydroxyacetone, nor one for converting 1,3-dihydroxyacetone to acetyl phosphoric acid. In the present invention, by means of site-directed mutation of BFD, a mutant of this enzyme is found. The mutant can catalyze formaldehyde to be condensed to hydroxyl acetaldehyde, which is first found and achieves the highly effective polymerization of the formaldehyde; meanwhile, by means of F/XPK, generation of acetyl phosphoric acid from the hydroxyl acetaldehyde or 1,3-dihydroxyacetone (DHA) is achieved; in combination with phosphotransacetylase (Pta), a route from the formaldehyde to acetyl coenzyme A is achieved in three steps, thereby creating a new pathway for assimilation of formaldehyde-synthesis of acetyl coenzyme A from formaldehyde in three steps. This pathway has a short route without a carbon loss and an input for ATP.

What is claimed is:

1. A method for preparing hydroxyl acetaldehyde and/or 1,3-dihydroxyacetone, comprising: catalyzing formaldehyde to be condensed to hydroxyl acetaldehyde and/or 1,3-dihydroxyacetone with a benzoylformate decarboxylase (BFD) mutant protein using formaldehyde as a substrate, wherein the BFD mutant protein comprises the amino acid sequence of SEQ ID NO: 1 with the exception of the mutations W86R and N87T, and optionally one or more mutations selected from the group consisting of L109G, L110E, H281V, Q282F, T377M, T380C, T380Y, and A460M, wherein the amino acid number corresponds to the amino acid sequence of SEQ ID NO: 1.

2. A method for producing acetyl phosphoric acid using formaldehyde, comprising: (i) catalyzing formaldehyde to be condensed to hydroxyl acetaldehyde and/or 1,3-dihydroxyacetone with a BFD mutant protein, using formaldehyde as a substrate; (ii) using the hydroxyl acetaldehyde and/or 1, 3-dihydroxyacetone obtained in (i) as a substrate to prepare acetyl phosphoric acid, wherein the BFD mutant protein comprises the amino acid sequence of SEQ ID NO: 1 with the exception of the mutations W86R and N87T, and optionally one or more mutations selected from the group consisting of L109G, L110E, H281V, Q282F, T377M, T380C, T380Y, and A460M, wherein the amino acid number corresponds to the amino acid sequence of SEQ ID NO:1.

3. A method for producing acetyl coenzyme A using formaldehyde, the method comprising: (i) catalyzing formaldehyde to be condensed to hydroxyl acetaldehyde and/or 1,3-dihydroxyacetone with a BFD mutant protein, using formaldehyde as a substrate; (ii) using hydroxyl acetaldehyde and/or 1,3-dihydroxyacetone obtained in (i) as a substrate to prepare acetyl phosphoric acid; and (iii) using the acetyl phosphoric acid as a substrate to prepare acetyl coenzyme A,
wherein the BFD mutant protein comprises the amino acid sequence of SEQ ID NO: 1 with the exception of the mutations W86R and N87T, and optionally one or more mutations selected from the group consisting of L109G, L110E, H281V, Q282F, T377M, T380C, T380Y, and A460M, wherein the amino acid number corresponds to the amino acid sequence of SEQ ID NO:1.

4. The method according to claim 2, wherein the step of preparing acetyl phosphoric acid comprises using hydroxyl acetaldehyde and/or 1,3-dihydroxyacetone as a substrate and catalyzed with a phosphoketolase (F/XPK) protein to generate acetyl phosphoric acid.

5. The method according to claim 3, wherein the step of preparing acetyl phosphoric acid comprises using hydroxyl acetaldehyde and/or 1,3-dihydroxyacetone as a substrate and catalyzed with a F/XPK protein to generate acetyl phosphoric acid.

6. The method according to claim 3, wherein the step of preparing acetyl coenzyme A comprises using acetyl phosphoric acid as a substrate and catalyzed with phosphotransacetylase to generate acetyl coenzyme A.

7. The method according to claim 1, wherein the BFD mutant protein performs its catalyzing function in the form of a crude enzyme liquid, lyophilized powders of a crude enzyme liquid, a pure enzyme or whole cells.

8. The method according to claim 4, wherein the F/XPK protein performs its catalyzing function in the form of a crude enzyme liquid, lyophilized powders of a crude enzyme liquid, a pure enzyme or whole cells.

9. The method according to claim 6, wherein the phosphotransacetylase performs its catalyzing function in the form of a crude enzyme liquid, lyophilized powders of a crude enzyme liquid, a pure enzyme or whole cells.

10. The method according to claim 7, wherein the crude enzyme liquid, the lyophilized powders of a crude enzyme liquid and the pure enzyme are all prepared and obtained in accordance wherein the method comprising: obtaining a recombinant cell by expressing the BFD mutant protein in a host cell; the crude enzyme liquid, the lyophilized powders of a crude enzyme liquid or the pure enzyme are obtained by lysing the recombinant cell;
the whole cells are all prepared and obtained in accordance with a method comprising: the BFD mutant protein is expressed in a host cell, and the obtained recombinant cell is the whole cell.

11. The method according to claim 10, wherein the recombinant cell is prepared and obtained in accordance with a method comprising: the recombinant cell expressing the BFD mutant protein is obtained by introducing a nucleic acid molecule capable of expressing the BFD mutant protein into the host cell, followed by induction culture.

12. The method according to claim 11, wherein the said nucleic acid molecule capable of expressing the BFD mutant protein is introduced into the host cell in the form of a recombinant vector; wherein the recombinant vector is a bacterial plasmid, phage, a yeast plasmid or a retrovirus packaging plasmid carrying the coding sequence of the BFD mutant protein; and/or the host cell is a prokaryotic cell or a lower eukaryotic cell.

13. The method according to claim 12, wherein the prokaryotic cell is bacteria; the lower eukaryotic cell is a yeast cell.

14. The method according to claim 13, wherein the bacteria are *Escherichia coli*.

15. The method according to claim 1, wherein the mutations are selected from the group consisting of: W86R-N87T-L109G-L110E, W86R-N87T-L109G-L110E-T377M, W86R-N87T-L109G-L110E-A460M, W86R-N87T-L109G-L110E-H281V-Q282F-A460M, W86R-N87T-T377M-T380C, and W86R-N87T-T377M-T380Y.

* * * * *

SEQUENCE LISTING

```
<160> NUMBER OF SEQ ID NOS: 6

<210> SEQ ID NO 1
<211> LENGTH: 528
<212> TYPE: PRT
<213> ORGANISM: Pseudomonas putida

<400> SEQUENCE: 1

Met Ala Ser Val His Gly Thr Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
        35                  40                  45

Cys Val Val Gly Ile Ala Asp Gly Tyr Ala Gln Ala Ser Arg Lys Pro
    50                  55                  60

Ala Phe Ile Asn Leu His Ser Ala Ala Gly Thr Gly Asn Ala Met Gly
65                  70                  75                  80

Ala Leu Ser Asn Ala Trp Asn Ser His Ser Pro Leu Ile Val Thr Ala
                85                  90                  95

Gly Gln Gln Thr Arg Ala Met Ile Gly Val Glu Ala Leu Leu Thr Asn
            100                 105                 110

Val Asp Ala Ala Asn Leu Pro Arg Pro Leu Val Lys Trp Ser Tyr Glu
        115                 120                 125

Pro Ala Ser Ala Ala Glu Val Pro His Ala Met Ser Arg Ala Ile His
    130                 135                 140
```

```
Met Ala Ser Met Ala Pro Gln Gly Pro Val Tyr Leu Ser Val Pro Tyr
145                 150                 155                 160

Asp Asp Trp Asp Lys Asp Ala Asp Pro Gln Ser His His Leu Phe Asp
            165                 170                 175

Arg His Val Ser Ser Ser Val Arg Leu Asn Asp Gln Asp Leu Asp Ile
                180                 185                 190

Leu Val Lys Ala Leu Asn Ser Ala Ser Asn Pro Ala Ile Val Leu Gly
        195                 200                 205

Pro Asp Val Asp Ala Ala Asn Ala Asp Cys Val Met Leu Ala
    210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Val Val Leu Val
                260                 265                 270

Ile Gly Ala Pro Val Phe Arg Tyr His Gln Tyr Asp Pro Gly Gln Tyr
            275                 280                 285

Leu Lys Pro Gly Thr Arg Leu Ile Ser Val Thr Cys Asp Pro Leu Glu
290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Ser Ser Arg Gln Leu
                325                 330                 335

Pro Thr Ala Ala Pro Glu Pro Ala Lys Val Asp Gln Asp Ala Gly Arg
                340                 345                 350

Leu His Pro Glu Thr Val Phe Asp Thr Leu Asn Asp Met Ala Pro Glu
            355                 360                 365

Asn Ala Ile Tyr Leu Asn Glu Ser Thr Ser Thr Thr Ala Gln Met Trp
370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
            435                 440                 445

Ile Phe Val Ile Met Asn Asn Gly Thr Tyr Gly Ala Leu Arg Trp Phe
450                 455                 460

Ala Gly Val Leu Glu Ala Glu Asn Val Pro Gly Leu Asp Val Pro Gly
465                 470                 475                 480

Ile Asp Phe Arg Ala Leu Ala Lys Gly Tyr Gly Val Gln Ala Leu Lys
            485                 490                 495

Ala Asp Asn Leu Glu Gln Leu Lys Gly Ser Leu Gln Glu Ala Leu Ser
                500                 505                 510

Ala Lys Gly Pro Val Leu Ile Glu Val Ser Thr Val Ser Pro Val Lys
            515                 520                 525

<210> SEQ ID NO 2
<211> LENGTH: 1584
<212> TYPE: DNA
<213> ORGANISM: Pseudomonas putida
```

<400> SEQUENCE: 2

```
atggcttctg ttcacggtac cacctacgaa ctgctgcgtc gtcagggtat cgacaccgtt      60
ttcggtaacc cgggttctaa cgaactgccg ttcctgaaag acttcccgga agacttccgt     120
tacatcctgg ctctgcagga agcttgcgtt gttggtatcg ctgacggtta cgctcaggct     180
tctcgtaaac cggctttcat caacctgcac tctgctgctg gtaccggtaa cgctatgggt     240
gctctgtcta cgcttggaa ctctcactct ccgctgatcg ttaccgctgg tcagcagacc      300
cgtgctatga tcggtgttga agctctgctg accaacgttg acgctgctaa cctgccgcgt     360
ccgctggtta atggtcttta cgaaccggct tctgctgctg aagttccgca cgctatgtct     420
cgtgctatcc acatggcttc tatggctccg cagggtccgg tttacctgtc tgttccgtac     480
gacgactggg acaaagacgc tgacccgcag tctcaccacc tgttcgaccg tcacgtttct     540
tcttctgttc gtctgaacga ccaggacctg gacatcctgg ttaaagctct gaactctgct     600
tctaacccgg ctatcgttct gggtccggac gttgacgctg ctaacgctaa cgctgactgc     660
gttatgctgg ctgaacgtct gaaagctccg gtttgggttg ctccgtctgc tccgcgttgc     720
ccgttcccga cccgtcaccc gtgcttccgt ggtctgatgc cggctggtat cgctgctatc     780
tctcagctgc tggaaggtca cgacgttgtt ctggttatcg tgctccggt tttccgttac     840
caccagtacg acccgggtca gtacctgaaa ccgggtaccc gtctgatctc tgttacctgc     900
gacccgctga agctgctccg tgctccgatg ggtgacgcta cgttgctga catcggtgct     960
atggcttctg ctctggctaa cctggttgaa gaatcttctc gtcagctgcc gaccgctgct    1020
ccggaaccgg ctaaagttga ccaggacgct ggtcgtctgc acccggaaac cgttttcgac    1080
accctgaacg acatggctcc ggaaaacgct atctacctga cgaatctac ctctaccacc     1140
gctcagatgt ggcagcgtct gaacatgcgt aacccgggtt cttactactt ctgcgctgct    1200
ggtggtctgg gtttcgctct gccggctgct atcggtgttc agctggctga accggaacgt    1260
caggttatcg ctgttatcgg tgacggttct gctaactact ctatctctgc tctgtggacc    1320
gctgctcagt acaacatccc gaccatcttc gttatcatga caacggtac ctacggtgct     1380
ctgcgttggt tcgctggtgt tctggaagct gaaaacgttc cgggtctgga cgttccgggt    1440
atcgacttcc gtgctctggc taaaggttac ggtgttcagg ctctgaaagc tgacaacctg    1500
gaacagctga aggttctct gcaggaagct ctgtctgcta aggtccggt tctgatcgaa      1560
gtttctaccg tttctccggg taaa                                           1584
```

<210> SEQ ID NO 3
<211> LENGTH: 825
<212> TYPE: PRT
<213> ORGANISM: Bifidobacterium adolescentis

<400> SEQUENCE: 3

```
Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80
```

-continued

```
Leu Ile Ala Asp His Gln Gln Asn Thr Val Ile Met Gly Pro Gly
                85                  90                  95
His Gly Gly Pro Ala Gly Thr Ala Gln Ser Tyr Leu Asp Gly Thr Tyr
            100                 105                 110
Thr Glu Tyr Phe Pro Asn Ile Thr Lys Asp Glu Ala Gly Leu Gln Lys
        115                 120                 125
Phe Phe Arg Gln Phe Ser Tyr Pro Gly Gly Ile Pro Ser His Tyr Ala
130                 135                 140
Pro Glu Thr Pro Gly Ser Ile His Glu Gly Gly Glu Leu Gly Tyr Ala
145                 150                 155                 160
Leu Ser His Ala Tyr Gly Ala Val Met Asn Asn Pro Ser Leu Phe Val
                165                 170                 175
Pro Ala Ile Val Gly Asp Gly Glu Ala Glu Thr Gly Pro Leu Ala Thr
            180                 185                 190
Gly Trp Gln Ser Asn Lys Leu Ile Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asn Glu Asp His
                245                 250                 255
Leu Ser Ile His Arg Arg Phe Ala Glu Leu Phe Glu Thr Val Phe Asp
            260                 265                 270
Glu Ile Cys Asp Ile Lys Ala Ala Ala Gln Thr Asp Asp Met Thr Arg
        275                 280                 285
Pro Phe Tyr Pro Met Ile Ile Phe Arg Thr Pro Lys Gly Trp Thr Cys
    290                 295                 300
Pro Lys Phe Ile Asp Gly Lys Lys Thr Glu Gly Ser Trp Arg Ser His
305                 310                 315                 320
Gln Val Pro Leu Ala Ser Ala Arg Asp Thr Glu Ala His Phe Glu Val
                325                 330                 335
Leu Lys Asn Trp Leu Glu Ser Tyr Lys Pro Glu Glu Leu Phe Asp Glu
            340                 345                 350
Asn Gly Ala Val Lys Pro Glu Val Thr Ala Phe Met Pro Thr Gly Glu
        355                 360                 365
Leu Arg Ile Gly Glu Asn Pro Asn Ala Asn Gly Gly Arg Ile Arg Glu
    370                 375                 380
Glu Leu Lys Leu Pro Lys Leu Glu Asp Tyr Glu Val Lys Glu Val Ala
385                 390                 395                 400
Glu Tyr Gly His Gly Trp Gly Gln Leu Glu Ala Thr Arg Arg Leu Gly
                405                 410                 415
Val Tyr Thr Arg Asp Ile Ile Lys Asn Asn Pro Asp Ser Phe Arg Ile
            420                 425                 430
Phe Gly Pro Asp Glu Thr Ala Ser Asn Arg Leu Gln Ala Ala Tyr Asp
        435                 440                 445
Val Thr Asn Lys Gln Trp Asp Ala Gly Tyr Leu Ser Ala Gln Val Asp
    450                 455                 460
Glu His Met Ala Val Thr Gly Gln Val Thr Glu Gln Leu Ser Glu His
465                 470                 475                 480
Gln Met Glu Gly Phe Leu Glu Gly Tyr Leu Leu Thr Gly Arg His Gly
                485                 490                 495
```

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ser Ser Met Asn Leu Leu Val Ser Ser His Val Trp
            530                 535                 540

Arg Gln Asp His Asn Gly Phe Ser His Gln Asp Pro Gly Val Thr Ser
545                 550                 555                 560

Val Leu Leu Asn Lys Cys Phe Asn Asn Asp His Val Ile Gly Ile Tyr
            565                 570                 575

Phe Pro Val Asp Ser Asn Met Leu Leu Ala Val Ala Glu Lys Cys Tyr
            580                 585                 590

Lys Ser Thr Asn Lys Ile Asn Ala Ile Ile Ala Gly Lys Gln Pro Ala
            595                 600                 605

Ala Thr Trp Leu Thr Leu Asp Glu Ala Arg Ala Glu Leu Glu Lys Gly
            610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
            645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Ala Lys Glu Asn Asn Glu
            675                 680                 685

Ala Leu Ser Asp Glu Glu Phe Ala Glu Leu Phe Thr Glu Asp Lys Pro
            690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
            725                 730                 735

Gln Gly Ser Thr Thr Thr Pro Tyr Asp Met Val Arg Val Asn Asn Ile
            740                 745                 750

Asp Arg Tyr Glu Leu Gln Ala Glu Ala Leu Arg Met Ile Asp Ala Asp
            755                 760                 765

Lys Tyr Ala Asp Lys Ile Asn Glu Leu Glu Ala Phe Arg Gln Glu Ala
            770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
            805                 810                 815

Thr Ala Thr Ala Gly Asp Asn Glu
            820                 825

<210> SEQ ID NO 4
<211> LENGTH: 2477
<212> TYPE: DNA
<213> ORGANISM: Bifidobacterium adolescentis

<400> SEQUENCE: 4
atgacctctc cggttatcgg taccccgtgg aaaaaactga acgcgccggt ttctgaagaa      60
gcgatcgaag gtgttgacaa atactggcgt gcggcgaact acctgtctat cggtcagatc     120
tacctgcgtt ctaacccgct gatgaaagaa ccgttcaccc gtgaagacgt taaacaccgt     180
ctggttggtc actggggtac caccccgggt ctgaacttcc tgatcggtca catcaaccgt     240

```
ctgatcgcgg accaccagca gaacaccgtt atcatcatgg gtccgggtca cggtggtccg      300
gcgggtaccg cgcagtctta cctggacggt acctacaccg aatacttccc gaacatcacc      360
aaagacgaag cgggtctgca gaaattcttc cgtcagttct cttacccggg tggtatcccg      420
tctcactacg cgccggaaac cccgggttct atccacgaag gtggtgaact gggttacgcg      480
ctgtctcacg cgtacggtgc ggttatgaac aacccgtctc tgttcgttcc ggcgatcgtt      540
ggtgacggtg aagcggaaac cggtccgctg gcgaccggtt ggcagtctaa caaactgatc      600
aacccgcgta ccgacggtat cgttctgccg atcctgcacc tgaacggtta caaaatcgcg      660
aacccgacca tcctgtctcg tatctctgac gaagaactgc acgagttctt ccacggtatg      720
ggttacgaac cgtacgagtt cgttgcgggt ttcgacaacg aagaccacct gtctatccac      780
cgtcgtttcg cggaactgtt cgaaaccgtt ttcgacgaaa tctgcgacat caaagcggcg      840
gcgcagaccg acgacatgac ccgtccgttc tacccgatga tcatcttccg taccccgaaa      900
ggttggacct gcccgaaatt catcgacggt aaaaaaaccg aaggttcttg gcgttctcac      960
caggttccgc tggcgtctgc gcgtgacacc gaagcgcact cgaagttct gaaaaactgg       1020 ctggaatctt acaaaccgga agaactgttc gacgaaaacg gtgcggttaa accggaagtt      1080
accgcgttca tgccgaccgg tgaactgcgt atcggtgaaa acccgaacgc gaacggtggt      1140
cgtatccgtg aagaactgaa actgccgaaa ctggaagact acgaagttaa agaagttgcg      1200
gaatacggtc acggttgggg tcagctggaa gcgacccgtc gtctgggtgt ttacacccgt      1260
gacatcatca aaacaacccc ggactctttc cgtatcttcg gtccggacga aaccgcgtct      1320
aaccgtctgc aggcggcgta cgacgttacc aacaaacagt gggacgcggg ttacctgtct      1380
gcgcaggttg acgaacacat ggcggttacc ggtcaggtta ccgaacagct gtctgaacac      1440
cagatggaag gtttcctgga aggttacctg ctgaccggtc gtcacggtat ctggtcttct      1500
tacgaatctt tcgttcacgt tatcgactct atgctgaacc agcacgcgaa atggctggaa      1560
gcgaccgttc gtgaaatccc gtggcgtaaa ccgatctctt ctatgaacct gctggtttct      1620
tctcacgttt ggcgtcagga ccacaacggt ttctctcacc aggacccggg tgttacctct      1680
gttctgctga caaatgctt caacaacgac cacgttatcg gtatctactt cccggttgac      1740
tctaacatgt gctgcgcgt tgcggaaaaa tgctacaaat ctaccaacaa atcaacgcg       1800 atcatcgcgg gtaaacagcc ggcggcgacc tggctgaccc tggacgaagc gcgtgcggaa      1860
ctggaaaaag gtgcggcgga atggaaatgg cgtctaacg ttaaatctaa cgacgaagcg       1920
cagatcgttc tggcggcgac cggtgacgtt ccgacccagg aaatcatggc ggcggcggac      1980
aaactggacg cgatgggtat caaattcaaa gttgttaacg ttgttgaccct ggttaaactg      2040 cagtctgcga aagaaaacaa cgaagcgctg tctgacgaag agttcgcgga actgttcacc      2100
gaagacaaac cggttctgtt cgcgtaccac tcttacgcgc gtgacgttcg tggtctgatc      2160
tacgaccgtc cgaaccacga caacttcaac gttcacggtt acgaagaaca gggttctacc      2220
accaccccgt acgacatggt tcgtgttaac aacatcgacc gttacgaact gcaggcggaa      2280
gcgctgcgta tgatcgacgc ggacaaatac gcggacaaaa tcaacgaact ggaagcgttc      2340
cgtcaggaag cgttccagtt cgcggttgac aacggttacg accacccgga ctacaccgac      2400
tgggtttact ctggtgttaa caccaacaaa cagggtgcga tctctgcgac cgcggcgacc      2460
gcgggtgaca acgaatg                                                    2477
```

```
<210> SEQ ID NO 5
<211> LENGTH: 715
<212> TYPE: PRT
<213> ORGANISM: Escherichia coli

<400> SEQUENCE: 5

Met Leu Leu Leu Cys Arg Leu Asn Arg Ser Gln Arg Asp Gly Val Asp
1               5                   10                  15

Asp Ile Val Asn Gln Cys Ala Thr Gly Gln Val Val Asn Arg Leu Ala
                20                  25                  30

His Thr Leu Gln His Arg Pro Asp Gly Asp Gln Val Gly Arg Thr Leu
            35                  40                  45

Tyr Arg Phe Val Gly Gly Val Thr Gly Val Gln Ile Arg Glu Asp Glu
    50                  55                  60

His Gly Ser Ala Thr Cys Asn Arg Arg Val Arg Arg Phe Gly Phe Arg
65                  70                  75                  80

Asn Val Ser His Tyr Arg Ser Val Val Leu Gln Arg Thr Val Asp His
                85                  90                  95

Gln Val Arg Thr Phe Phe Leu Arg Gln Thr Ser Cys Phe Ala Asn Phe
            100                 105                 110

Phe Tyr Val Ala Thr Cys Thr Arg Ser Thr Gly Val Gly Glu His
    115                 120                 125

Ser Asn Ala Arg Phe Asp Thr Glu Gly Arg Ser Gly Ile Ser Gly Leu
130                 135                 140

Asn Arg Asp Phe Cys Gln Leu Phe Ser Gly Arg Ile Arg Val Asp Arg
145                 150                 155                 160

Thr Val Thr Val Asn Val Asn Leu Phe Arg Gln His Glu Glu His
                165                 170                 175

Gly Arg Tyr Gln Gly Ala Ala Arg Cys Ser Phe Asp Gln Leu Gln Arg
            180                 185                 190

Arg Thr Asp Gly Val Cys Gly Ser Val Asn Ser Thr Gly Asn Gln Thr
    195                 200                 205

Ile Asn Phe Ile Leu Phe Gln His Gln Arg Thr Glu His His Val Val
210                 215                 220

Phe Gln Leu Phe Ala Gly Asn Gly Phe Gly His Ala Phe Val Leu Thr
225                 230                 235                 240

Gln Phe Asp Gln Thr Thr Asn Ile Ala Phe Ala Asn His Phe Trp Ile
                245                 250                 255

Asn Asp Phe Asn Pro Cys Thr Gln Phe Tyr Thr Leu Arg Arg Cys Asn
            260                 265                 270

Thr Val Asp Leu Cys Arg Ile Thr Gln Gln Tyr Ala Ser Cys Asp Thr
    275                 280                 285

Thr Phe Ser Thr Asp Ser Gly Cys Phe Asn Gly Thr Arg Phe Val Thr
290                 295                 300

Phe Arg Gln Tyr Asp Thr Phe Ala Arg Phe Ala Arg Lys Phe Ser Gln
305                 310                 315                 320

Leu Ile Thr Glu Arg Arg Arg Gln Thr Thr Ala Ala Leu Arg Ser
                325                 330                 335

Gly Ser Gln Arg Phe Asp Pro Val Ser Val Asp Val Ser Asn Val
            340                 345                 350

Phe Leu Asn Phe Leu Asp Thr Leu Val Ile Val Asn Arg Asn Phe Gln
    355                 360                 365

Val Glu Ala Leu Gln Ala Gln Arg Gly Leu Pro Gly Val Gly Val His
370                 375                 380
```

```
His Lys Tyr Arg Gln Ala Gly Ser Glu Ser Thr Phe Ala Gln Phe Arg
385                 390                 395                 400

Asn Ala Arg Val His Phe Val Ala Ala Ser Gln Gln Gln Gly Thr Asp
            405                 410                 415

Phe Tyr Ala Val His Gly Cys Gln Ala Ser Gly His Gln His Val Arg
            420                 425                 430

Thr Val Cys Gly Ser His Gln Gln Arg Thr Gly Thr Glu Val Leu Gln
            435                 440                 445

His Val Arg Asn Ala Ala Cys Ala Glu Ser Asp Gly Phe Asn Ala Ala
            450                 455                 460

Ser Ile Asp Val Ala Phe Val Asp Asp Gly Arg Ile Gln Val Ala Ser
465                 470                 475                 480

His Ile Asp Arg Thr Ser Arg Asp Gln Val Lys Ala Pro Arg His Ser
            485                 490                 495

Ala Glu Asn Arg Gln Arg Ala Gly Phe Leu Gln Leu Arg Arg Ile Asn
            500                 505                 510

Ile Val Tyr Phe Ser Phe Gly Arg Val Val Glu Asn Leu Gly Gln Ile
            515                 520                 525

Arg Ala Ser Thr Thr Leu Phe Ile Asn Arg Cys Val Gln Phe Val Asn
530                 535                 540

Asp Asn Ala Gly Asp Val Gly Val Phe Gly Thr Ala Glu Ala Val Ala
545                 550                 555                 560

Gly Gln Phe Asp Thr Leu Phe Gln Leu Phe Arg Gly Val Ser Ala Leu
            565                 570                 575

Arg His Asn Glu Asp Asp Phe Arg Ile Gln Arg Phe Ser Asp Phe Val
            580                 585                 590

Val Gln Arg Leu Gly Lys Leu Val Leu Thr Cys Arg Asp Gln Thr Phe
            595                 600                 605

Asn Gln Asn Asp Phe Ser Val Phe Gly Val Ser Val Val Cys Asp
610                 615                 620

Asp Leu Phe His Gln His Ile Phe Leu Ile Ala Gly Lys Gln Thr Phe
625                 630                 635                 640

Asn Val Ala His Phe Gln Arg Phe Ser Gly Arg Arg Gly Gly Arg Val
            645                 650                 655

Arg Thr His Asp Ser Arg Ser Leu Ile Gly Arg Ile Ala Thr Gly Thr
            660                 665                 670

Arg Leu Ser Asp Arg Phe Glu Asn Ala Gln Thr Asn Ala Phe Ala Phe
            675                 680                 685

His Cys Thr Asp His Ala Lys Ala Asp Ala Gly Gln Thr Asp Ala Gly
            690                 695                 700

Ser Gly Arg Asp Gln His Asn Asn Thr Gly His
705                 710                 715

<210> SEQ ID NO 6
<211> LENGTH: 2145
<212> TYPE: DNA
<213> ORGANISM: Escherichia coli

<400> SEQUENCE: 6
atgctgctgc tgtgcagact gaatcgcagt cagcgcgatg gtgtagacga tatcgtcaac      60
cagtgcgcca cgggacaggt cgttaaccgg cttgcgcata ccctgcagca tcggcccgat     120
ggagatcagg tcggcagaac gctgtaccgc tttgtaggtg gtgttaccgg tgttcagatc     180
cgggaagatg aacacggtag cgcgaccctg aaccggagag ttcggcgctt tggatttcgc     240
```

```
aacgtcagcc attaccgcag cgtcgtactg cagcggaccg tcgatcatca ggtcaggacg    300
ttttccctgc gccagacgag ttgcttcgcg aacttttct acgtcgctac ctgcaccaga    360
agtaccggtg gagtaggaga gcatagcaac gcgcggttcg ataccgaagg ccgcagcgga    420
atcagcggac tgaatcgcga tttctgccag ctgttcagcg gtcggatccg ggttgatcgc    480
acagtcaccg taaacgtaaa cctgttccgg cagcagcatg aagaacacgg aagataccag    540
ggagctgccc ggtgcagttt tgatcagctg cagcggcgga cggatggtgt ttgcggtagt    600
gtgaacagca ccggaaacca gaccatcaac ttcatcctgt tccagcatca gcgtaccgag    660
caccacgttg tcttccaact gttcgcgggc aacggtttcg gtcatgcctt tgttcttacg    720
cagttcgacc agacgaccaa catagctttc gcgaaccact tctggatcaa cgatttcaat    780
ccctgcaccc agttctacac cctgagacgt tgcaacacgg ttgatctctg ccggattacc    840
cagcagtacg caagttgcga taccacgttc agcacagata gcggctgctt taacggtacg    900
cggttcgtca ccttccggca gtacgatacg tttgcccgct ttgcgcgcaa gttcagtcag    960
ctgataacgg aacgcaggcg gagacagacg acggctgcgc tcagaagtgg cagtcagaga   1020
ttcgatccag tcagcgttga tgtagttagc aacgtattcc tgaactttct cgatacgctc   1080
gtgatcgtca accggaactt ccaggttgaa gctctgcagg ctcagagagg tctgccaggt   1140
gttggtgttc accataaata ccggcaggcc ggtagcgaaa gcacgttcgc acagtttaga   1200
aatgcgcgcg tccatttcgt agccgccagt cagcagcagg gcaccgattt ctacgccgtt   1260
catggctgcc aggcaagcgg ccaccagcac gtcaggacgg tctgcggaag tcaccagcag   1320
agaaccggca cggaagtgct ccagcatgtg cggaatgctg cgtgcgcaga aagtgacgga   1380
tttaacgcgg cgagtattga tgtcgccttc gttgatgatg gtcgcattca ggtggcgagc   1440
catatcgatc gcacgagtcg cgatcaggtc aaagctccac ggcacagcgc cgagaaccgg   1500
cagcgggctg gattcttgca gcttcgccgg atcaacattg tttactttag ctttggaaga   1560
gtcgtcgaaa atctcggaca gatccgggcg agtacgaccc tgttcatcaa ccggtgcgtt   1620
cagtttgtta acgataacgc cggtgatgtt ggtgttttg gcaccgccga agctgttgcg   1680
ggtcagttcg atacgctctt tcagctgttc cggggtgtca gtgccctgag acataacgaa   1740
gacgatttcc gcattcagcg ttttagcgat ttcgtagttc agagactggg caaactggtg   1800
cttacgtgtc gggaccagac cttcaaccag aacgacttca gcgtctttgg tgttagcgtg   1860
gtagtttgcg acgatctctt ccatcagcac atctttctga ttgctggaaa gcagaccttc   1920
aacgtagctc attttcagcg gttcagcggc cgtcgtggtg gaagagttcg cacgcacgat   1980
agtcgtagtc tgatcgggcg catcgccacc ggtacgcggc tgagcgatag gtttgaaaac   2040
gctcagacga acgcctttgc gttccattgc acggatcacg ccaaggctga cgctggtcag   2100
accgacgctg gttccggtag ggatcagcat aataatacgg gacac                   2145
```